| United States Patent [19] | [11] | 4,440,855 |
|---|---|---|
| Horwath et al. | [45] | Apr. 3, 1984 |

[54] PROCESS FOR PREPARING L-GLUCOSONE

[75] Inventors: Robert O. Horwath, Westport; William J. Colonna, Wilton, both of Conn.

[73] Assignee: Nabisco Brands, Inc., Parsippany, N.J.

[21] Appl. No.: 393,290

[22] Filed: Jun. 30, 1982

[51] Int. Cl.$^3$ .................... C12P 19/02; C12N 9/04; C12R 1/645; C12R 1/66; C12R 1/69
[52] U.S. Cl. .................................. 435/105; 435/190; 435/911; 435/913; 435/918
[58] Field of Search .................... 435/105, 148, 190

[56] References Cited

U.S. PATENT DOCUMENTS

| 4,246,347 | 1/1981 | Neidleman et al. | 435/105 |
| 4,262,032 | 4/1981 | Levin | 426/658 |
| 4,321,323 | 3/1982 | Maselli et al. | 435/105 |
| 4,351,902 | 9/1982 | Neidleman et al. | 435/105 |

*Primary Examiner*—Lionel M. Shapiro
*Attorney, Agent, or Firm*—R. Kornutik

[57] ABSTRACT

Process for preparing L-glucosone from L-glucose by contacting L-glucose with glucose-2-oxidase derived from a microorganism selected from the group consisting of the genera Polyporus, Aspergillus, Oudemansiella, Radulum, Lenzites, Irpex, Pellicularia, Armillaria, Schizophyllum, and Corticium.

2 Claims, No Drawings

PROCESS FOR PREPARING L-GLUCOSONE

BACKGROUND OF THE INVENTION

This invention relates to a process for preparing L-glucosone alone or in admixture with other L-sugars, such as L-fructose.

L-sugars are useful as sweetening agents because, as disclosed in U.S. Pat. No. 4,262,032, they are sweet like the D-sugars, but unlike D-sugars, L-sugars are either not metabolized by the body or are metabolized to a lesser extent than the D-sugars. These features make L-sugars desirable as sweeteners for individuals wishing to reduce caloric-intake or for individuals unable to metabolize common sugar sweetening agents without detrimental effects, e.g., diabetics. Another advantage associated with L-sugars include the absence of an objectionable aftertaste commonly experienced with artificial sweeteners such as saccharin and the cyclamates. However, as desirable as the L-sugars are in the foregoing respects, their relative scarcity in nature, particularly L-glucose and L-fructose, the laevo counterparts of the two monosaccharide sweeteners most commonly used today, has prevented their widespread use in foods and beverages or even their being considered for use in such products.

U.S. Pat. No. 4,246,347 to Neidleman, et al., the contents of which are incorporated by reference herein, describes a two-step process for producing D-fructose from D-glucose. The first step is the enzymatic conversion of D-glucose to D-glucosone by employing glucose-2-oxidase or carbohydrate oxidase. The second step is the chemical hydrogenation of D-glucosone to D-fructose.

At the present, there are no teachings in the prior art which indicate that glucose-2-oxidase will convert L-glucose to L-glucosone.

SUMMARY OF THE INVENTION

In accordance with the present invention, L-glucose is oxidized to L-glucosone by employing glucose-2-oxidase isolated from or present in a strain of microorganism of the genera Polyporus, Oudemansiella, Aspergillus, Radulum, Lenzites, Irpex, Pellicularia, Armillaria, Schizophyllum and Corticium.

DESCRIPTION OF THE PREFERRED EMBODIMENTS

The starting L-sugar for the process herein, L-glucose, a naturally occurring sugar, can be obtained by chemical conversion of L-arabinose, a naturally occurring sugar which is available in significant quantities from sugar beet pulp by the method described in Chemical Abstracts: 142135v, Vol. 75, 1971 (Czech. Patent No. 137,537), the contents of which are incorporated by reference herein. According to this method, dry sugar beet pulp is treated with sulfuric acid to obtain an extract solution which is subsequently fermented, evaporated and filtered. L-arabinose is thereafter crystallized from the resulting filtrate.

L-glucose can be produced from L-arabinose by the method of Sowden and Fischer, J.A.C.S., Vol. 69 (1947), pp. 1963–1965, the contents of which are incorporated by reference herein. In accordance with this method, L-arabinose is condensed with nitromethane in the presence of sodium methoxide to provide sodium salts of the nitroalcohols. The sodium salts are readily converted to the corresponding sugars by means of the Nef reaction. The Sowden-Fischer conversion of L-arabinose to the L-glucose starting material of this invention is represented by the following equations:

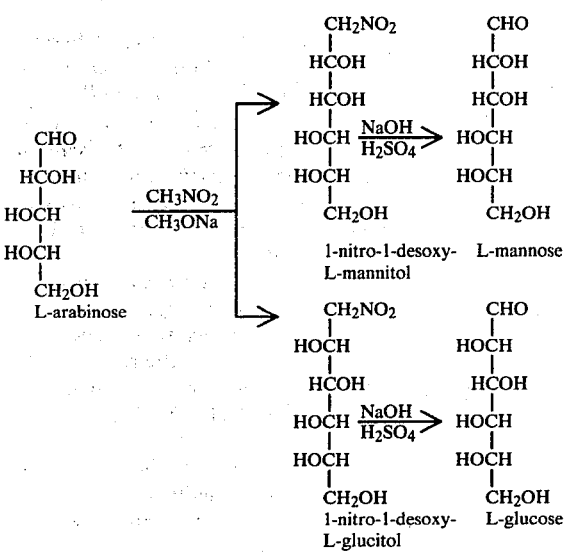

In addition to the Sowden-Fischer method, L-glucose can also be made by the Kiliani-Fischer synthesis which is described in, amongst others, *Organic Chemistry* by Morrison and Boyd (2d ed. 1966), pp. 990–991, the contents of which are incorporated by reference herein. According to the Kiliani-Fischer method, L-arabinose is converted into two glyconic acids of the next higher carbon number by condensation with hydrocyanic acid and hydrolysis of the resulting cyanohydrins. The glyconic acids are then reduced to the corresponding aldoses. The Kiliani-Fischer synthesis of L-glucose from L-arabinose is illustrated by the following equations:

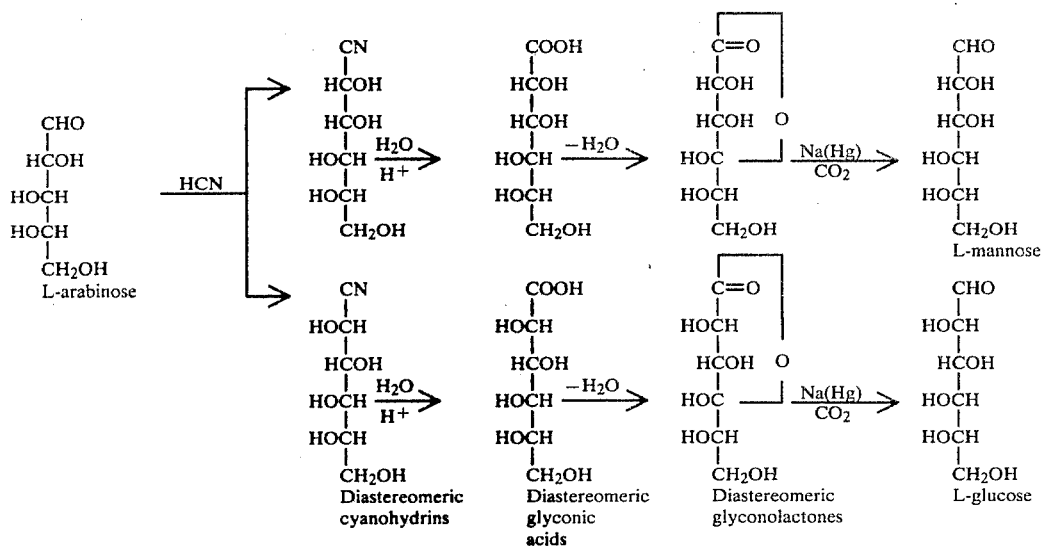

Both synthetic procedures provide L-glucose in admixture with L-mannose. The L-glucose can be separated from the L-mannose, e.g., by differential crystallization in either a free or derivatized state, or by separation using ion-exchange techniques.

To obtain the carbohydrate oxidase utilized herein, one can use any microorganism which produces glucose-2-oxidase, e.g., *Polyporus obtusus, Aspergillus oryzae, Oudemansiella mucida, Radulum casearium, Lenzites trabea, Irpex flavus, Polyporus versicolor, Pellicularia filamentosa, Armillaria mellea, Schizophyllum commune,* or *Corticium caeruleum* and their equivalents. However, *Polyporus obtusus* is preferred since it is known to be a good source of glucose-2-oxidase.

The microorganisms utilized in the present invention are maintained on yeast/malt extract agar slants containing yeast extract, malt extract, agar, peptone, glucose and distilled water, at a pH within the range of 5 to 8, preferably between 6 and 7, at about room temperature, i.e., within the range of 20° C. to 35° C., preferably about 25° C.

The slant-grown microorganisms are then employed to inoculate a yeast/malt extract medium as described above excluding the presence of agar, and grown for about five to ten days with shaking at about room temperature, preferably about 25° C.

The mycelia of the microorganism, wherein the enzyme is contained, are collected by art recognized procedures, e.g., collection by filtration on a coarse filter paper supported on a Buchner funnel, and washed with water. The mycelia can be frozen and stored until needed.

The L-glucose oxidation is carried out by utilizing art recognized procedures to immobilize the mycelia containing glucose-2-oxidase or to rupture the mycelia, for example, through homogenization or ultra-sonic treatment. If the mycelia are ruptured to release the intracellular oxidase, a cell-free extract containing the enzyme is obtained by known methods, e.g., centrifugation. The extract can be further purified by methods generally known in the art, including polyethylene glycol fractionation and acid fractionation. The extracellular enzyme can be immobilized in accordance with known and conventional procedures. For example, the enzyme, can be immobilized on various particulate silica material including glass or ceramic-based materials, natural or synthetic polymers such as cellulose, e.g., diethylaminoethyl cellulose, and various known organic polymer supports known in the art.

The oxidation of L-glucose to L-glucosone is effected in an aqueous enzyme solution at a pH within the range of 3 to 8, preferably at about a neutral pH to obviate the need for appropriate buffers, containing a source of oxygen at about 15° C. to 35° C., preferably at room temperature, for a length of time which can be readily determined experimentally. The reaction temperature selection will be predicated on the thermal stability of the enzyme system employed, the more thermally stable systems permitting higher reaction temperatures. Of course, the reaction time will, in part, be determined by the reaction temperature. As would be expected, the higher the temperature, the shorter the reaction time period for the desired degree of reaction. In enzymatic reactions of the present type, equilibrium will be reached in reasonable time periods, usually ranging from as little as 30 minutes up to several hours, and even longer. As is recognized in this art, the progress of the reaction can be followed by removal of aliquots from the reaction mixture and analyzing for product and/or starting substrate, thus, permitting optimization of reaction parameters for the specific enzyme system employed. The enzyme system may vary depending on the microorganism from which the enzyme is obtained, and the method of isolation and purification, if employed.

In addition to the above, methods known to those familiar with the art are used to remove the hydrogen peroxide formed during the oxidation process because hydrogen peroxide impairs the functioning of the enzyme by oxidizing certain critical sites on the enzyme molecule. These methods include decomposition of the $H_2O_2$ by the enzyme, catalase, decomposition by decomposing matrices, e.g., manganese oxide or carbon black, as the immobilizing support for the oxidase enzyme, and known chemical means.

In one embodiment of the present invention, the oxidation process is carried out in a reactor having a first zone in which the oxidation occurs separated from a second zone by a hydrogen peroxide permeable membrane. An example of using a semi-permeable membrane to remove $H_2O_2$ during the enzymatic oxidation of D-glucose to D-glucosone is described in U.S. Pat. No. 4,321,323 to Maselli, et al., the contents of which are incorporated by reference herein. Due to the relative concentrations of $H_2O_2$ on each side of the membrane, the $H_2O_2$ tends to migrate to the second zone as the oxidation reaction proceeds. The addition of a reducing agent to the second zone is desired to reduce the concentration of $H_2O_2$ in the second zone, thereby, causing the equilibrium to shift in favor of greater migration of $H_2O_2$ to said zone.

Once the oxidation reaction is essentially completed, i.e., approximately 99% of the L-glucose has been converted, the enzyme is removed from the reaction mixture by art recognized procedures, e.g., by denaturing the enzyme and removing the denatured protein by centrifugation, or separation of immobilized enzyme by physical means, e.g., filtration.

Since the conversion of L-glucose to L-glucosone is substantially complete, the L-glucosone without prior concentration or isolation, can be catalytically hydrogenated to L-fructose by methods known in the art. Suitable catalysts include catalysts comprising one or more metals or metallic compounds having hydrogen activity, e.g., metals from Groups IB, IIB and VIII of the Periodic Table. The catalysts may be supported, and employed alone or in admixture with promoters. Generally, the hydrogenation is carried out at ambient temperature and pressure. This hydrogenation is essentially complete, and L-fructose is recovered by known methods substantially free of other saccharides.

EXAMPLE

A. Isolation of glucose-2-oxidase

Mycelial pads of *Polyporus obtusus* are grown for 7 days at 25° C. on yeast/malt extract agar slants containing 3 g of yeast extract, 3 g of malt extract, 20 g of agar, 5 g of peptone, and 10 g of glucose in 1 L of water at pH 6.4.

Thereafter, the microorganisms grown on the agar slants are used to inoculate a 125 ml Erlenmeyer flask containing the yeast/malt extract medium described above, but without agar added, then cultivated for 9 days on a rotary shaker at 25° C. The mycelia are collected by vacuum filtering the culture through #541 Whatman paper supported on a Buchner funnel.

The mycelia are then twice washed with 0.05 M potassium phosphate buffer (pH 7.0), and homogenized for three minutes in a Waring blender which contains 70 ml of 0.05 M potassium phosphate buffer (pH 7.0). The mixture is centrifuged for 20 minutes at 6000 rpm to obtain a supernatant portion containing the glucose-2-oxidase.

The supernatant is purified by adding 19 g of polyethylene glycol (weight 4000), and stirring the solution for 30 minutes. The suspension is then centrifuged at 7000 rpm for 20 minutes, and the supernatant removed. To the remaining precipitate is added 15 ml of 0.2 M sodium chloride and 15 ml of 0.05 M potassium phosphate (pH 7.0), and the mixture is vortexed. After the solution stands for 30 minutes, a precipitate forms. The mixture is centrifuged at 14000 rpm for 20 minutes, and the supernatant containing the oxidase is decanted off.

To immobilize the enzyme on agarose, the supernatant is first dialyzed against 500 ml of distilled water overnight. 5 ml of 0.1 M sodium bicarbonate (pH 8.0) and 5 g of Activated CH-Sepharose 4B, washed and reswelled on a sintered glass filter using 500 ml of 1 mM HCl, are then added to the dialyzed solution. The resulting gel suspension is mixed with an end-over-end mixer for 1 hour at 25° C. The gel suspension is then washed three times, the first time with 40 ml of 0.1 M sodium bicarbonate (pH 8.0), the second time with 40 ml of 0.05 M Tris buffer (pH 8.0) containing 0.5 M sodium chloride, and the third time with 0.5 M sodium formate buffer (pH 4.0) containing sodium chloride.

B. Oxidation of L-glucose to L-glucosone

Oxygen gas is bubbled through a stirred reaction mixture containing 2 g of L-glucose, 20 ml of aqueous phosphate buffer (pH 7.0), the agarose-immobilized glucose-2-oxidase prepared in step A and 3 mg of catalase at about 25° C. for 4 hours or until the conversion is essentially completed. The immobilized enzyme is then removed by filtration.

We claim:

1. A process for oxidizing L-glucose to L-glucosone which comprises contacting L-glucuose with glucose-2-oxidase produced by a microorganism selected from the group consisting of genera Polyporus, Aspergillus, Oudemansiella, Radulum, Lenzites, Irpex, Pellicularia, Armillaria, Schizophyllum and Corticium.

2. A process according to claim 1, wherein the microorganism is *Polyporus obtusus, Aspergillus oryzae, Oudemansiella mucida, Radulum casearium, Lenzites trabea, Irpex flavus, Polyporus versicolor, Pellicularia filamentosa, Armillaria mellea, Schizophyllum commune,* and *Corticium caeruleum.*

* * * * *